US005834259A

United States Patent [19]

Pantaleone et al.

[11] Patent Number: 5,834,259

[45] Date of Patent: Nov. 10, 1998

[54] PROCESS AND COMPOSITION FOR PREPARING D-ASPARTIC ACID

[75] Inventors: David P. Pantaleone, Buffalo Grove; Ian G. Fotheringham, Vernon Hills; Jennifer L. Ton, Palatine, all of Ill.

[73] Assignee: Monsanto Company, St. Louis, Mo.

[21] Appl. No.: 738,890

[22] Filed: Oct. 28, 1996

[51] Int. Cl.[6] .......... C12P 13/20

[52] U.S. Cl. .......... 435/109; 435/232; 435/280

[58] Field of Search .......... 435/109, 280, 435/232

[56] References Cited

PUBLICATIONS

APS Japanese ABS J62–87088 (Apr. 21, 1997) Koyama et al.

Williamson, J. M. and Brown, G. M., J. Biol. Chem., vol. 254, No. 16, pp. 8074–8082 (1979).

Nakano, Y. and Kitaoka, S., J. Biochem., vol. 70, pp. 327–334 (1971).

Cronan, J. E., Jr., J. Bacteriol., vol. 141, No. 3, pp. 1291–1297 (1980).

Cronan, J. E., Jr., Anal. Biochem., vol. 103, No. 2, pp. 377–380 (1980).

Merkel, W. K. and Nichols, B. P., FEMS Microbiol. Lett., vol. 143, No. 2–3 pp. 247–252 (1996).

*Primary Examiner*—Herbert J. Lilling
*Attorney, Agent, or Firm*—Fitzpatrick, Cella, Harper & Scinto

[57] ABSTRACT

A process and composition for preparing D-aspartic acid and β-alanine from D,L-aspartic acid, wherein a solution of D,L-aspartic acid or a salt thereof is contacted with a composition having an L-aspartate-α-decarboxylase activity of greater than 100 μmol L-aspartate used per hour per gram of cells, under appropriate conditions to produce D-aspartic acid and β-alanine.

25 Claims, 8 Drawing Sheets

PROCESS AND COMPOSITION FOR PREPARING D-ASPARTIC ACID

BACKGROUND OF THE INVENTION

1. Field of the Invention

This invention relates to a method for preparing D-aspartic acid from racemic aspartic acid. More particularly, the invention relates to a method of preparing D-aspartic acid and β-alanine by enzymatic decarboxylation of racemic aspartic acid.

2. Description of the Related Art

The L-aspartate-α-decarboxylase enzyme catalyzes the production of β-alanine from L-aspartic acid. Nakano et al. demonstrated the activity of the enzyme in the form of a crude extract from *E. coli*, B. Nakano, Y. et al., J. Biochem. Vol. 70, pages 327–334 (1971). Williamson et al. further investigated the activity of the enzyme in *E. coli* purified to apparent homogeneity. Williamson, J. et al., J. Biol. Chem., Vol. 254(16), pages 8074–8082 (August 1979). These disclosures do not demonstrate the production of the enzyme in any useful amount beyond experimental curiosity. As discussed more fully below, this invention utilizes a composition having between 100 and 2000 times the L-aspartate-α-decarboxylase activity of that disclosed in the Nakano et al. and Williamson et al. references.

U.S. Pat. No. 5,019,509 to Rozzell discloses methods and compositions for the production of L-alanine and derivatives thereof. Rozzell, however, discloses the gene encoding the aspartate-β-decarboxylase and its use to produce L-alanine. U.S. Pat. Nos. 5,552,317 and 5,552,318 to Houng, et. al. discloses methods for preparing optically active amino acids and esters thereof using lipase from wheat germ or *Candida lipolytica*. In contrast, the process of this invention is not a common resolution such as the Houng et al. methods, where it is common that resolution of amino acids is actually performed on derivatives of the amino acids, thus requiring additional chemical steps. Most often, racemic esters are treated with esterases/lipases or N-acetyl-amino acids are treated with acylases.

Other resolution procedures are known that use an amidase acting on racemic amino acid amides where the enzyme is just specific for one isomer. See, U.S. Pat. No. 4,880,737. However, the present invention provides a much more simple process because there are no additional chemical modifications to prepare the substrate.

This invention provides a facile route to produce two highly useful compounds from an abundant source, D,L-aspartate. D-aspartic acid and its derivatives have been widely documented in pharmaceuticals. These uses include, but are not limited to, the inhibition of arginiosuccinate synthetase activity which is useful to prevent or treat sepsis or cytokine-induced systemic hypotension and as immunosuppressive agents. Other uses of D-aspartic acid include taste modifying compositions for foods and a new sweetener, Alitame™, under development by Pfizer. In addition, β-alanine is used in the synthesis of pantothenic acid, which is necessary for coenzyme A synthesis. β-alanine is also known to be used as a chiral synthon for the synthesis of α-substituted β-amino acids. Derivatives of β-alanine have been used as a buffer in the electroplating industry.

SUMMARY OF THE INVENTION

A racemic mixture of aspartic acid isomers (D and L) are incubated with a microorganism containing the panD gene encoding the enzyme L-aspartate-α-decarboxylase (E.C. 4.1.1.11) or a suitable source of enzyme. The enzyme catalyzes the following reaction:

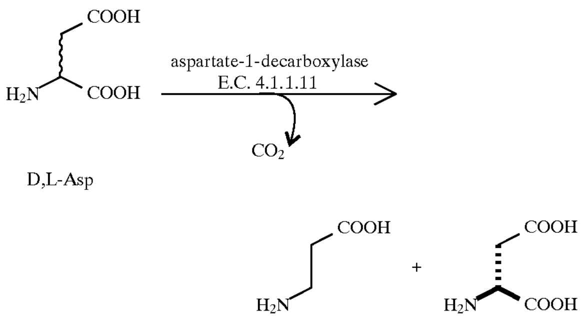

D,L-Asp

β-Ala

D-Asp

The enzyme stereospecifically decarboxylates L-aspartate to β-alanine and $CO_2$ whereas D-aspartate remains unreacted. Because this reaction is essentially irreversible with the release of $CO_2$, a high conversion of product is realized. This reaction can be carried out under mild conditions, i.e., room temperature and neutral pH, thus making this process very environmentally friendly and highly desirable.

DETAILED DESCRIPTION

Figure 1:
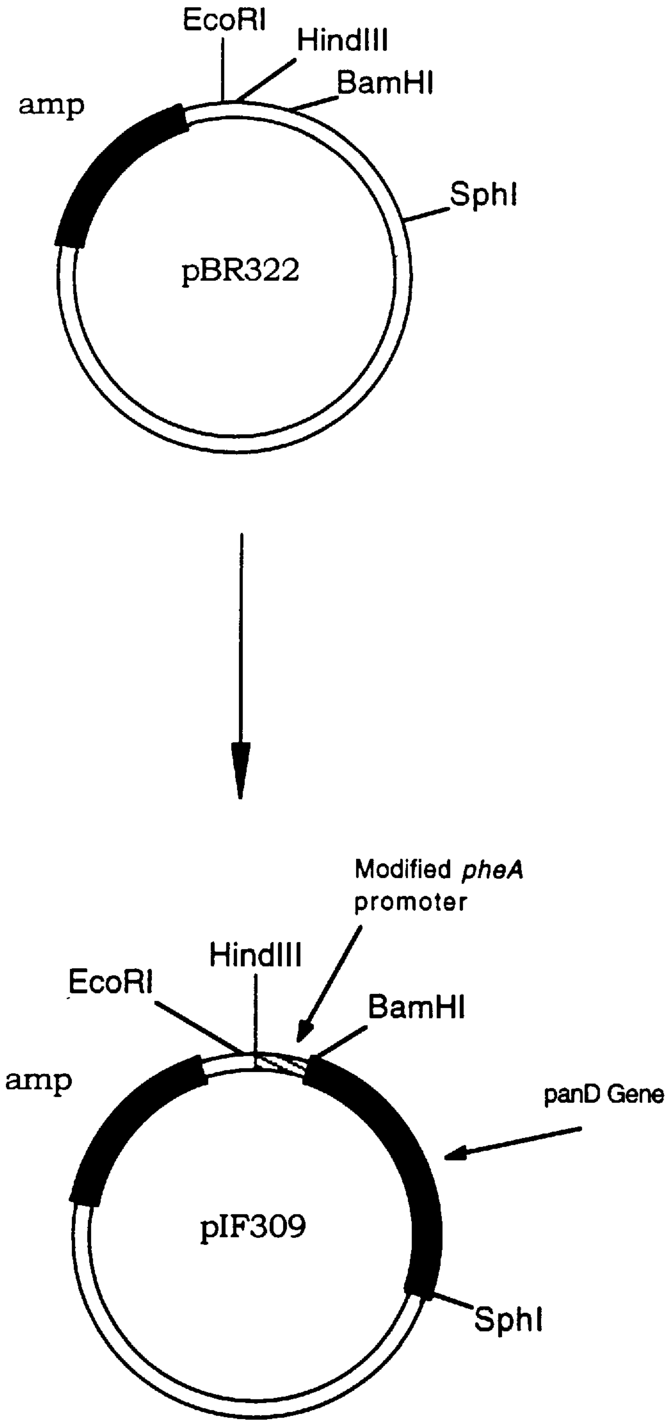
FIG. 1 shows the production of Plasmid pIF309.

The present invention provides a process for preparing D-aspartic acid from D,L-aspartic acid which comprises incubation of a solution of D,L-aspartic acid or a salt thereof with a composition comprising cells of a microorganism or extracts thereof, wherein the composition has an L-aspartate-α-decarboxylase activity of greater than 100 μmol L-aspartate used per hour per gram of cells, under appropriate conditions to produce D-aspartic acid and β-alanine.

The enzyme L-aspartate-α-decarboxylase, also referred to herein as L-aspartate-1-decarboxylase, aspartate-1-decarboxylase or E.C. 4.1.1.11, is used in the present invention to prepare D-aspartic acid from racemic aspartic aid according to the following reaction scheme:

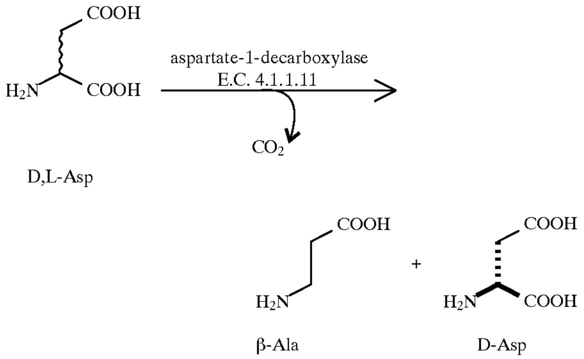

The substrate and reaction products are alternatively referred to herein by their acid and salt forms. For example, the substrate D,L-aspartic acid is also referred to herein as D,L-aspartate. Those of ordinary skill in the art recognize that the form, and therefore the nomenclature, of an acid differs depending on the pH of the solution in which it is found. As will be discussed more fully below, the process of this invention is useful over a wide pH range which provides for the use of both acid and salt forms of substrate. For the purposes of the present disclosure, the acid and salt-based nomenclature used herein is intended to be synonymous.

The panD gene of *E. coli* K12, encoding the enzyme was cloned into *E. coli* on a multi copy plasmid vector which is used in a whole cell biotransformation system to produce β-alanine and D-aspartic acid. "Whole cell biotransformation system" refers to the use of cells containing the enzyme which have not been extracted to purify the enzyme but which may be ultrafiltered or otherwise separated from the fermentation media and added directly to the solution to catalyze the reaction to produce β-alanine and D-aspartic acid. Other "Systems" can be used to practice the claimed invention without departing from the scope of the invention. Such methods include, but are not limited to, the use of immobilized cell fractions, immobilized whole enzyme or enzyme fraction. Methods of forming cell fractions and purified enzyme and enzyme fractions are well known to those of ordinary skill in the art. Preferred methods of immobilization are discussed below.

The enzyme L-aspartate-α-decarboxylase, also referred to herein as L-aspartate-1-decarboxylase or EC 4.1.1.11, catalyzes the removal of the alpha carboxyl group from L-aspartate to produce β-alanine.

The present invention also provides a composition comprising cells of a microorganism or extracts thereof, wherein the composition has an L-aspartate-α-decarboxylase activity of greater than 100 μmol L-aspartate used per hour per gram of cells.

In one embodiment the composition comprises cells or extracts of cells of a microorganism transformed with a vector comprising the panD gene which encodes for the L-aspartate-α-decarboxylase enzyme. For example the vector can be a plasmid, such as pIF309 described herein. The vector is then used to transform a microorganism such as a bacterium, for example *E. coli*. In a preferred embodiment the composition comprises cells or extracts of cells of *E. coli* NS3291 ATCC Accession NO. 98675.

The composition of this invention has an L-aspartate-α-decarboxylase activity of greater than 100 μmol L-aspartate used per hour per gram of cells, and preferably, between about 100 and 2000 μmol L-aspartate used per hour per gram of cells. The enzyme activity of the claimed compositions is calculated using the activity demonstrated in Williamson et al. noted above as a reference point. In that reference, the crude extract showed an activity of 6700 U from 400 grams of cells where 1 U was equal to 1 nmol of $CO_2$ liberated per minute at 42° C. Thus, 16.75 U/g cells is equal to 16.75 nmol $CO_2$ liberated per minute per gram of cells. Assuming complete conversion of one mol of L-aspartate to one mol of β-alanine and one mol of $CO_2$, 16.75 nmol L-aspartate used per minute per gram of cells would result in approximately 1 μmol L-aspartate utilized per hour per gram cells. As demonstrated in the Examples herein, the composition of the present invention provides an activity of greater than 100 times the activity of the enzyme preparations known in the prior art. From Table III of the Williamson paper the specific activity of the purified enzyme was 650 U/mg protein. Assuming that 50% of the total cell protein has this activity, the present process and composition provide L-aspartate-α-decarboxylase activity up to 2000 μmol L-aspartate used per hour per gram of cells. In a preferred embodiment the composition has an L-aspartate-α-decarboxylase activity of between about 100 and 2000 μmol L-aspartate used per hour per gram of cells. In another embodiment, the composition has an L-aspartate-α-decarboxylase activity of between about 100 and 1000 μmol L-aspartate used per hour per gram of cells.

Cloning of the L-aspartate-α-decarboxylase gene can be accomplished by the isolation of a DNA fragment encoding the polypeptide carrying the L-aspartate-α-decarboxylase activity from a suitable donor microorganism, and incorporating the DNA fragment into a suitable vector, known to those of ordinary skill in the art. Suitable donor microorganisms include all microorganisms carrying a gene encoding a polypeptide which catalyzes the α-decarboxylation of L-aspartate to β-alanine. Examples include, but are not limited to, bacteria from the genus *Escherichia coli* ("*E. coli*"), including *E. coli* B, *E. coli* K12, *E. coli* NIHJ and *E. coli* Tennessee; *Proteus vulgaris; Bacterium cadaveris; Azotobacter vinelandii; Rhizobium leguminosarum; R. trifolii*; or bacterium from the genus Bacillus.

Suitable cloning vectors useful in the practice of this invention normally contain an origin of replication and a selectable marker to maintain the stability of the vector in the host cell and to facilitate the identification of transformants. A description of some methods and materials useful in the cloning of the L-aspartate-α-decarboxylase gene can be found in Molecular Cloning: A Laboratory Manual [T. Maniatis, E. Fritsch, and J. Sambrook, Cold Spring Harbor Laboratory (1982)] and references therein, which are hereby incorporated by reference.

The DNA fragment encoding the polypeptide displaying L-aspartate-α-decarboxylase activity is then expressed. The general strategy for expression of the L-aspartate-α-decarboxylase gene involves the ligation of the DNA fragment encoding the polypeptide displaying L-aspartate-α-decarboxylase activity into an expression vector suitable for the desired host cell, many examples of which are well known in the art. Suitable expression vectors are normally characterized by the presence of an origin of replication, a promoter or other transcription enhancing sequences, a ribosome binding site, and a transcriptional termination sequence. The expression vector may also include a gene conferring resistance to an antibiotic as a selectable marker; however, plasmids containing any other gene encoding a protein required by the host microorganism for growth and viability may be used as a selectable marker, if desired.

Examples of promoters useful in recombinant DNA constructions include, but are not limited to, tryptophan, alkaline phosphatase, beta-galactosidase, beta-lactamase, and $P_L$ promoter systems; and hybrid promoter systems composed of components or structures from two or more known promoter systems such as tac. While these are the most common promoters used in bacterial host strains, other strains and microbial species amenable to genetic manipulation and other promoters useful in those host strains may also be used.

After the ligation, the resultant vector of this invention contains the L-aspartate-α-decarboxylase gene in operative association with a promoter such that host cells transformed with the vector are capable of directing the production of L-aspartate-α-decarboxylase. Suitable hosts for transforming with the vector include any microorganism, for example a bacterium, which allows for the expression of the gene encoding L-aspartate-α-decarboxylase. Examples include, but are not limited to, bacteria of the genera *Escherichia, Bacillus*, Klebsiella, Pseudomonas, Salmonella, Proteus, Azotobacter, and Rhizobium.

In a preferred embodiment of this invention, the host strain for expression of the L-aspartate-α-decarboxylase gene is any strain of *E. coli*, in particular *E. coli* W3110, and the promoter system is the modified pheA promoter described in U.S. Pat. No. 5,120,837 (Fotheringham et al.) the contents of which are incorporated herein by reference. Expression of the gene is thus accomplished by ligation of the gene into a vector for gene expression in the chosen host strain. In an especially preferred embodiment of this invention, the vector used for the expression of the L-aspartate-α-decarboxylase gene in *E. coli* is pBR322 or a plasmid which is derived from pBR322, such as pIF309. The plasmid pBR322 contains genes encoding ampicillin and tetracycline resistance, allowing the facile identification of transformed cells.

If the preferred embodiment pIF309 is used, expression of the enzyme is constitutive. If a heat sensitive promoter is used, for example the λcI857 repressor/promoter system, induction of the synthesis of L-aspartate-α-decarboxylase can be accomplished by a temperature shift, for example, raising the fermentation temperature from 30° C. to 40° C. L-aspartate-α-decarboxylase enzyme would be expected to be produced at levels of from about 5% to about 40% of the total protein in the cell, thus yielding whole cells containing an enzyme composition with very high L-aspartate-α-decarboxylase activity.

It is not critical to this invention whether the expression of the gene results in enzyme produced intracellularly or extracellularly, since the desired product may be conveniently recovered and, if desired, further purified in either case by methods known to those of ordinary skill in the art. In a separately preferred embodiment, the gene can be incorporated into a thermostable microorganism to identify mutations in the gene which enhance the thermal stability of the enzyme thus allowing for the operation of this process at elevated temperatures.

In the practice of this invention, the cells producing elevated levels of L-aspartate-α-decarboxylase enzyme may be contacted with a solution containing D,L-aspartic acid or a salt thereof, with the resulting conversion of at least a portion of the L-aspartic acid in the reaction mixture to β-alanine, liberating $CO_2$ and leaving D-aspartic acid. The cells may be permeabilized to facilitate diffusion of the substrates and products into and out of the cells. This permeabilization can be accomplished by treating cells with a low concentration of a surfactant, including but not limited to Tween 80®, Triton X-100®, Nonidet P40®, cetylpyridinium chloride, deoxycholic acid, hexadecyltrimethylammonium bromide or benzalkonium chloride. Further, organic solvents, including but not limited to N,N-dimethylformamide (DMF), dimethyl sulfoxide (DMSO), ethanol or acetone at low concentrations have also been used to increase permeabilization. L-aspartate-α-decarboxylase may also be added to the D,L-aspartate-containing reaction mixture in the form of cell extracts containing crude, partially purified, or purified L-aspartate-α-decarboxylase enzyme. Cell extracts are prepared by methods known to those skilled in the art which provide for cell disruption and recovery of the enzyme. Cell disruption, can be accomplished by mechanical or non-mechanical means. Most often, for bacterial suspensions mechanical devices such as a French pressure cell, ultrasonication, bead mill or Manton-Gaulin homogenizer is used with the specifics of the method known to those of ordinary skill in the art. See, Scopes, R. K. "Protein Purification", (1982) (Springer-Verlag, N.Y.). The reaction using the cell extract is then carried out in similar fashion to the whole cell method discussed above.

The L-aspartate-α-decarboxylase-containing cells, or extracts thereof or purified enzyme or enzyme fractions, may also be immobilized, if desired. Immobilization methods which may be used in the practice of this invention include well-known methods such as entrapment in polymeric gels, covalent attachment, crosslinking, adsorption, and encapsulation. Some examples of these methods are described by A. M. Klibanov in Science, 219:722–727 (1983) and the references therein and in Methods in Enzymology (1976), Volume 44, (K. Mosbach editor) which are hereby incorporated by reference. In one method of immobilization disclosed in U.S. Pat. No. 5,019,509, a support material containing at least 20% by weight of silica or alumina is contacted with aminoalkyl compound such as an aminoalkyl silane, polyethyleneimine, or a polyalkylamine, followed by activation with glutaraldehyde. The enzyme-containing solution is then contacted with the activated support to produce an immobilized enzyme composition having L-aspartate-α-decarboxylase activity. Other immobilization supports useful in the practice of this invention include, but are not limited to, porous glass and porous ceramics, bentonite, diatomaceous earth, charcoal Sepharose® and Sepharose® derivatives, cellulose and cellulose derivatives, polyacrylamide and polyacrylamide derivatives, polyazetidine, alginate, carrageenan, and Chromosorb®. Sepharose® (Pharmacia Fine Chemicals, Uppsala Sweden) is a bead-formed gel prepared from agarose. The manufacturer's product literature reports that in its natural state, agarose occurs as part of the complex mixture of charged and neutral polysaccharides referred to as agar. The agarose used to make Sepharose® is obtained by a purification process which removes the charged polysaccharides to give a gel with only a very small number of residual charged groups. Those of ordinary skill in the art will appreciate that a number of other materials suitable for the immobilization of cells or extracts derived therefrom may also be useful for the immobilization of the L-aspartate-α-decarboxylase of the present invention. These supports can be activated, if desired, by techniques well-known in the art.

The reaction to produce D-aspartic acid utilizing cells containing L-aspartate-α-decarboxylase, or compositions comprising extracts derived from said cells, is carried out by contacting a solution containing D,L-aspartate with the L-aspartate-α-decarboxylase under conditions permitting the conversion of at least a portion of the L-aspartate to β-alanine. The concentration of D,L-aspartate is not critical in this reaction and concentrations as high as 2M would be anticipated to be useful. In a preferred embodiment of the process the cells or extracts of cells contact an aqueous solution D,L-aspartate having a concentration of 0.5M. In a separately preferred embodiment, the solution of D,L-aspartate has a concentration of 1.0M.

The enzymatic reactions of this invention are carried out at temperatures in the range of from about 4° C. to about 70° C., and preferably at temperatures ranging from about 20° C. to about 60° C. In a preferred embodiment, the temperature of the reaction is ambient temperature. For the purposes of this invention, "ambient temperature" means that no methods or devices are employed to either raise or lower the temperature of the reaction vessel from the temperature of the reaction vessel at rest in its natural environment. The optimal pH for the reaction ranges from about 2.0 to about 12.0, and more preferably from about 4.0 to about 9.0, with a pH of 7.0 being most preferred.

The D-aspartate and β-alanine may be separated and recovered by methods known in the art, or the D-aspartate/β-alanine mixture may be recovered or used directly as a mixture. The L-aspartate-α-decarboxylase compositions of this invention are further applicable to the production of β-alanine or β-alanine/D-aspartate mixtures containing radioactive or non-radioactive isotopic labels. Such products are readily produced by using an appropriately labelled aspartate precursor, and/or by carrying out the reaction in the presence of isotopically labelled solvent. Examples of isotopic labels which can be incorporated into the β-alanine and/or D-aspartate products include, but are not limited to, $^{14}C$, $^{13}C$, $^{13}N$, $^{15}N$, $^{2}H$, $^{3}H$, $^{17}O$, and $^{18}O$.

The invention will now be further illustrated by the following examples, which are not intended, and should not be interpreted, to limit the scope of the invention which is defined in the claims which follow thereafter.

EXAMPLE 1

Preparation of Plasmid pIF309

The pad gene encoding L-aspartate-1-decarboxylase was isolated from the chromosome of *E. coli* K12 by PCR using the following methods.

A. Chromosomal DNA Preparation

*E. coli* strain W3110 was obtained from the Coli Genetic Stock Center (Yale University, Newhaven, Conn.) The strain was recovered as directed in the supplier's instructions and cultured overnight with shaking in a 50 ml volume of Luria Broth at 37° C. in a 500 ml flask. A 10 ml aliquot of culture was centrifuged at 10,000×G for 4 minutes. The supernatant fluid was discarded and the pellet resuspended in 1 ml of a solution containing 50 mM Tris/HCl at pH 8.0, 10 mM EDTA and 100 μg/ml RNase A (Sigma). This was incubated for 10 minutes at room temperature. To this was added 2 ml of solution containing 0.4% (w/v) sodium dodecyl sulfate ("SDS") and 100 μg/ml protease K (Sigma). This was incubated for 20 minutes at 37° C. To this was added sodium acetate at pH 5.2 to a final concentration of 300 mM. This solution was then extracted 3 times with an equal volume of phenol at 37° C. and precipitated with 2.5 volumes of ethanol. The DNA was then removed with a sterile loop and redissolved in 400 μl of 300 mM sodium acetate at pH 5.2. The DNA was then re-precipitated in 2.5 volumes of ethanol, removed as before, dried and taken up in 500 μl of 10 mM Tris pH 8.0 and 1 mM EDTA. The final concentration was approximately 200 μg/ml.

B. Amplification of panD by PCR

Amplification of the *E. coli* panD gene by PCR was accomplished using a 0.2 ml MicroAmp™ reaction tube (Perkin Elmer, Norwalk, Conn.) to which was added 100 ng *E. coli* chromosomal DNA prepared as above, 2 μl each of dATP, dGTP, dCTP and dTTP (10 mM each), 10 μl of buffer comprising 15 mM $MgCl_2$, 500 mM KCl, 100 mM Tris pH 8.3, and 0.01% (w/v) gelatin, 5 U of Taq DNA polymerase (AmpliTaq™) and 5 μl of a 10 nmol/ml solution of each of the following oligonucleotide primers which were synthesized according to known methods using an Applied Biosystems 380B DNA synthesizer.

(MB1682)

5' CGC GGA TCC ACT ATG ATT CGC ACG ATG CTG CAG GGC 3'

(MG1683)

5' CAG CGT GCA TGC TCA AGC AAC CTG TAC CGG AAT CGC 3'

The reaction was carried out in a Perkin Elmer 9600™ PCR Thermal Cycler (Perkin Elmer). Amplification was carried out by pre-heating at 94° C. for 3 minutes followed by 30 cycles of denaturation at 94° C. for 30 seconds, annealing at 50° C. for 30 seconds and extension at 72° C. for 2 minutes. The reaction mixture was then stored at 4° C.

C. Cloning of panD

The amplified panD gene was cloned on a plasmid vector derived from plasmid pBR322. This plasmid was named pIF309. The fragment containing the panD gene was digested to completion with the restriction enzymes BamHI and SphI and ligated between the unique BamHI and SphI sites of the vector which had been similarly cleaved. Between the HindIII and BamHI sites was inserted a synthetic DNA fragment which carried a modified version of the *E. coli* K12 pheA promoter region. This fragment was completely synthesized on an Applied Biosystems 380B DNA synthesizer and derived from that characterized in co-owned U.S. Pat. No. 5,120,837 to Fotheringham et al. such that the sequence was as follows:

HindIII

AAGCTTTTTTGTTGACAGCGTGAAAA-CAGTACGGGTATAATACT AAAGTCACAAG-GAGGATCC

BamHI

Plasmid pIF309 is shown in FIG. 1. Restriction digests were carried out using enzymes supplied by New England Biolabs and used according to the manufacturer's specifications (NEB, Beverly, Mass.). Ligation of DNA fragments was carried out using a ligation kit supplied by Takara Biochemicals (Panvera Corp., Madison Wis.) according to the manufacturer's specifications.

Expression of panD was determined by biological assay of L-aspartate-1-decarboxylase activity in extracts prepared from cultures of strain NS3291 grown as described below.

EXAMPLE 2

Production and Fermentation of *E. coli* Strain NS3291

Plasmid pIF309 was used to transform *E. coli* strain W3110, using conditions described in U.S. Pat. No. 5,354,672 the contents of which are hereby incorporated by reference, resulting in the strain NS3291. Strain NS3291 was deposited with the American Type Culture Collection (ATCC) 12301 Parklawn Drive, Rockville, Md. 20852, USA. The strain is designated ATCC Accession No. 98675.

The strain NS3291 was inoculated into a 2800 ml Fernbach flask containing 1 L of the following growth medium:

| | | |
|---|---|---|
| Potassium phosphate (dibasic) | 13 | g |
| Potassium phosphate (monobasic) | 2 | g |
| Ammonium phosphate | 4 | g |
| Ferric ammonium citrate | 0.24 | g |
| Yeast extract | 2 | g |
| Magnesium sulfate (7 · $H_2O$) | 1 | g |
| Water | 930 | ml |
| After Sterilization the following were added: | | |
| Glucose (50% W/V stock) | 70 | ml |
| Ampicillin | 0.2 | g |

The flask was incubated on a shaker incubator at 37° C. with agitation. The strain was grown to 800–1100 Klett units and used to inoculate the fermentor. The fermentor was a Biolafite 78–100 (St. Germain-en Laye, France) 20 L. The fermentor was operated under the following conditions:

| | | |
|---|---|---|
| Agitation | 500 | rpm |
| Temperature | 37° | C. |
| Back Pressure | 0.7 | Bar |
| pH (adjusted with $NH_3$) | 7.2 | |
| Aeration | 1 | vvm |
| Set Volume | 10 | L |
| Inoculation | 100 | ml |
| Run Time | 16 | hr |

The fermentation medium was comprised of the following, per liter of medium unless otherwise noted:

| | | |
|---|---|---|
| Magnesium Sulfate (7 · $H_2O$) | 5.35 | g |
| Ferric ammonium citrate | 0.13 | g |
| Potassium phosphate (dibasic) | 4.6 | g |
| Manganese sulfate | 0.023 | g |
| Potassium iodide | 0.74 | mg |
| Nickel sulfate | 0.74 | mg |
| Antifoam (Mazur Mazu DF204) | 0.4 | ml |
| Yeast extract | 5 | g |
| L-aspartic acid | 10 | g |
| Tap water | 10 | L |

Prior to inoculation, glucose was added to a concentration of 25 g/l. After the initial glucose was completely depleted, glucose was fed at a variable rate to achieve less than 1 g/l for the remaining time for a total of 290 grams of glucose in 16 hours. The final volume of the tank was 12.2 L. The fermentation reached 10,352 Klett units and a dry cell weight of 24.2 g/l. The fermentor broth was cooled to below 10° C. and ultrafiltered using a hollow fiber cartridge (500, 000 Mol Wt. cutoff) to a dry cell weight of 158 g/l. The concentrated cell cream was stored at 4° C.

This strain was used in the following Examples.

EXAMPLE 3

Bioconversion of D/L-aspartate with L-aspartate-α-decarboxylase 66.5 g (0.5M) D/L-aspartate (Sigma, A-9006) was weighed into a 2 L beaker and the pH adjusted to 7.0 with 10N NaOH. The volume was brought to 963 ml with deionized $H_2O$. 137 ml of cells (NS 3291, described above) were added at a packed cell volume ("PCV") of 7.31 g/10 ml cells resulting in a final volume of 1.1 L. Samples (approximately 1 ml each) were removed over time, centrifuged and the supernatant fluid was analyzed by HPLC for D- and L-aspartic acid content.

In all of the Examples herein, D- and L-aspartic acid isomers were quantified by HPLC using the following precolumn derivatization method. Aspartic acid was converted into diastereomers using ortho-phthalaldehyde and N-acetyl-L-cysteine. Separation of the diastereomers was achieved on a Supelcosil™ LC-18DB, 3$\mu$, 150×4.6 mm column using a mobile phase of A: 20% methanol/80% triethylamine phosphate and B: methanol, and a step gradient as follows:

| Time (min) | A (%) | B (%) |
|---|---|---|
| 6.5 | 100 | 0 |
| 7.0 | 40 | 60 |
| 11.5 | 40 | 60 |
| 12.0 | 100 | 0 |

The derivatization was carried out automatically using a Hewlett-Packard 1090M chromatograph and detection was at 338 nm (bandwidth 4) and a flow rate of 1.0 ml/minute. Retention times were 4.19 minutes and 4.54 minutes for D-aspartic acid and L-aspartic acid, respectively.

Samples from bioconversions were centrifuged to remove cells in a microcentrifuge and the supernatant fluid diluted appropriately such that the value determined from the HPLC fell within the linear region of the standard curve. These dilutions were usually between 1:100 and 1:200, made with deionized water.

Throughout the Examples the terms "D-Asp" and "L-Asp" are used as short hand notation for the respective isomers of aspartic acid.

TABLE 1

| | Time (hr) | D-Asp (mg/ml) | D-Asp (%) | L-Asp (mg/ml) | L-Asp (%) |
|---|---|---|---|---|---|
| 0 | 0.0000 | 29.300 | 100.00 | 28.870 | 100.00 |
| 1 | 5.5000 | 29.320 | 100.07 | 12.050 | 41.739 |
| 2 | 24.500 | 29.250 | 99.829 | 0.17000 | 0.58885 |
| 3 | 26.500 | 27.740 | 94.676 | 0.12000 | 0.41566 |
| 4 | 32.500 | 28.090 | 95.870 | 0.060000 | 0.20783 |
| 5 | 47.500 | 28.060 | 95.768 | 0.030000 | 0.10391 |
| 6 | 52.000 | 28.390 | 96.894 | 0.020000 | 0.069276 |
| 7 | 68.000 | 25.520 | 87.099 | 0.43000 | 1.4894 |

Figure 2:
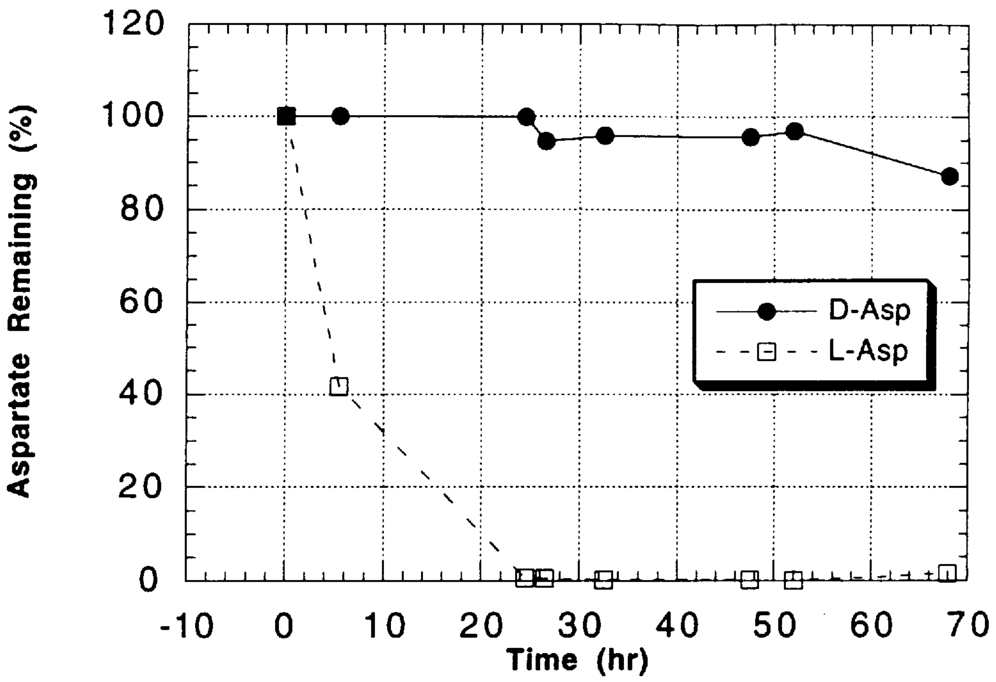
FIG. 2 shows the bioconversion of D,L-aspartate substrate solution to D-aspartate and β-alanine, as demonstrated by the reduction in the amount of L-aspartate remaining in solution, catalyzed by the L-aspartate-α-decarboxylase enzyme preparation of the invention.

The data in Table 1 are presented graphically in FIG. 2. At approximately 24 hours, the percent L-aspartate remaining is essentially negligible, about 0.17 mg/ml. The enzyme activity of the composition used in the bioconversion is calculated as follows:

$$0.5M\ \text{D,L-Asp} = 0.25M\ \text{D-Asp} + 0.25M\ \text{L-Asp}$$

$$\frac{0.25\ \text{mol}}{\text{L}} \times 1.1\ \text{L} = 0.275\ \text{mol L-Asp}$$

$$275\ \text{mmol L-Asp} = \frac{275 \times 10^3\ \mu\text{mol L-Asp used/24 hours}}{100\ \text{g cells}}$$

which equals 114.6 $\mu$mol L-aspartic acid used per hour per gram cells, or more than 100 times the enzyme activity known in the prior art.

The enantiomeric enrichment at this time is calculated as follows:

$$\frac{29.25 - 0.17}{29.25 + 0.17} = 0.988\ \text{D-Asp}$$

Following the whole-cell bioconversion reaction the cells were removed by centrifugation or ultrafiltration. The pH of the cell-free bioconversion mixture was adjusted with mineral acid, usually sulfuric acid, to a pH where D-aspartic acid precipitates as a solid and the β-alanine remains in solution, typically between pH 2.0 and 2.5. The solid was collected by filtration or other means and washed with cold water to afford D-aspartic acid. Recovery was between 50% and 90%.

EXAMPLE 4

Re-Treatment of Supernatant Fluid with Fresh Cells

In this Example the supernatant fluid from Example 3 was re-treated with fresh cells. The reaction from Example 3, stopped at 68 hours, was centrifuged for 45 minutes in a GS-3 rotor at 7000 rpm. The supernatant fluid, 990 ml, was separated from the cells. 963 ml of this supernatant fluid was mixed with 137 ml fresh cells and placed in a 2 L fermentor. Bioconversion took place with mixing at 300 rpm, without automatic pH control and at a temperature of 37° C. Samples, approximately 1 ml, were removed over time and analyzed as in Example 3.

TABLE 2

| | Time (hr) | D-Asp (mg/ml) | D-Asp (%) | L-Asp (mg/ml) | L-Asp (%) |
|---|---|---|---|---|---|
| 0 | 0.0000 | 21.450 | 100.00 | 0.43000 | 100.00 |
| 1 | 2.7500 | 21.350 | 99.534 | 0.11000 | 25.581 |
| 2 | 13.500 | 21.190 | 98.788 | 0.090000 | 20.930 |
| 3 | 15.000 | 20.770 | 96.830 | 0.080000 | 18.605 |
| 4 | 19.500 | 21.480 | 100.14 | 0.090000 | 20.930 |
| 5 | 23.500 | 20.880 | 97.343 | 0.070000 | 16.279 |
| 6 | 39.000 | 19.080 | 88.951 | 0.10000 | 23.256 |
| 7 | 47.000 | 17.280 | 80.559 | 0.16000 | 37.209 |
| 8 | 51.750 | 17.010 | 79.301 | 0.23000 | 53.488 |
| 9 | 68.500 | 14.900 | 69.464 | 0.55000 | 127.91 |

Figure 3:
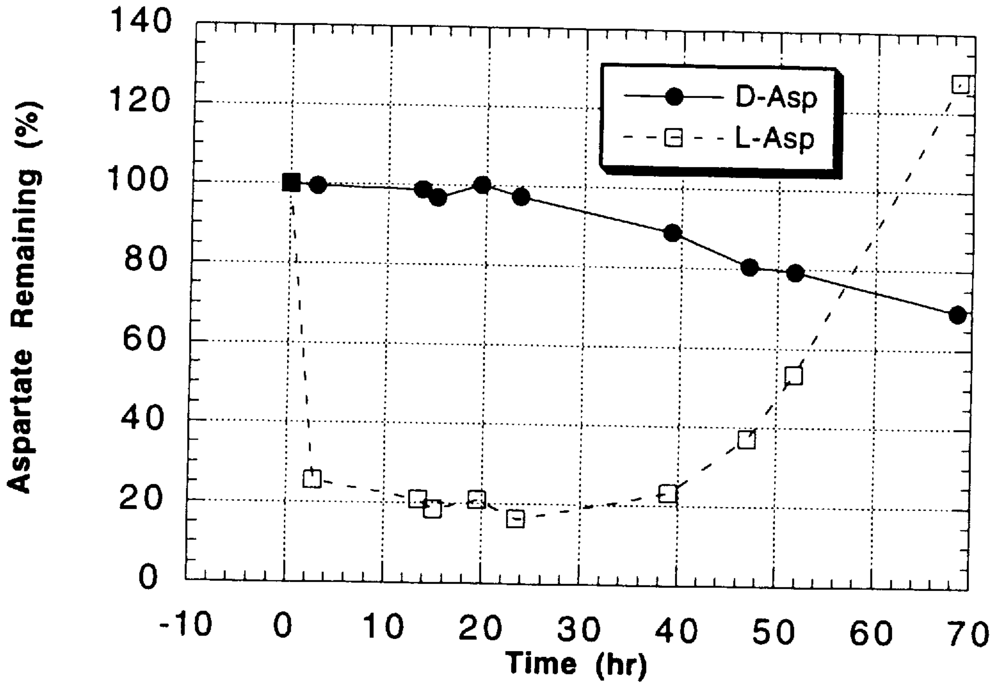
FIG. 3 shows the activity of fresh cells of the L-aspartate-α-decarboxylase enzyme preparation on the supernatant fluid left after completion of the reaction demonstrated in FIG. 2.

The data in Table 2 are represented graphically in FIG. 3. Although the concentration of L-aspartic acid at t=0 was not high (0.43 mg/ml), it was essentially reduced to nothing (0.07 mg/ml) by 23.5 hours. It is believed that the increases shown for concentration of L-aspartic acid after 23.5 hours is due to evaporation, although concomitant synthesis from extraneous enzymes could not be ruled out. At the end of the reaction (68.5 hours) there was only 0.55 mg/ml L-aspartic acid.

EXAMPLE 5

Re-use of Cells

Cells that had already been used in Example 3 were put in fresh substrate to determine if they were still active.

Fresh D/L-aspartate substrate was prepared as previously described in Example 3. The cells from Example 3 were resuspended in deionized $H_2O$ and made up to 100 ml. The pH of the substrate (900 ml, 0.5M D/L-Asp) was adjusted to 7.0 with NaOH. After placing in the 2 L fermentor, the cells (100 ml) were added. There was no pH control and deionized $H_2O$ was used for substrate. Samples were removed over time, centrifuged and the supernatant fluid diluted appropriately for both D- and L-aspartic acid determination. Temperature was set at 37° C.

TABLE 3

| | Time (hr) | D-Asp (mg/ml) | D-Asp (%) | L-Asp (mg/ml) | L-Asp (%) |
|---|---|---|---|---|---|
| 0 | 0.0000 | 30.850 | 100.00 | 24.700 | 100.00 |
| 1 | 6.2500 | 30.820 | 99.903 | 17.130 | 69.352 |
| 2 | 15.250 | 29.870 | 96.823 | 15.620 | 63.239 |
| 3 | 25.750 | 28.250 | 91.572 | 10.870 | 44.008 |
| 4 | 28.000 | 27.980 | 90.697 | 9.5300 | 38.583 |
| 5 | 44.250 | 25.000 | 81.037 | 4.4200 | 17.895 |
| 6 | 63.500 | 21.760 | 70.535 | 0.98000 | 3.9676 |
| 7 | 65.000 | 20.340 | 65.932 | 0.95000 | 3.8462 |

Figure 4:
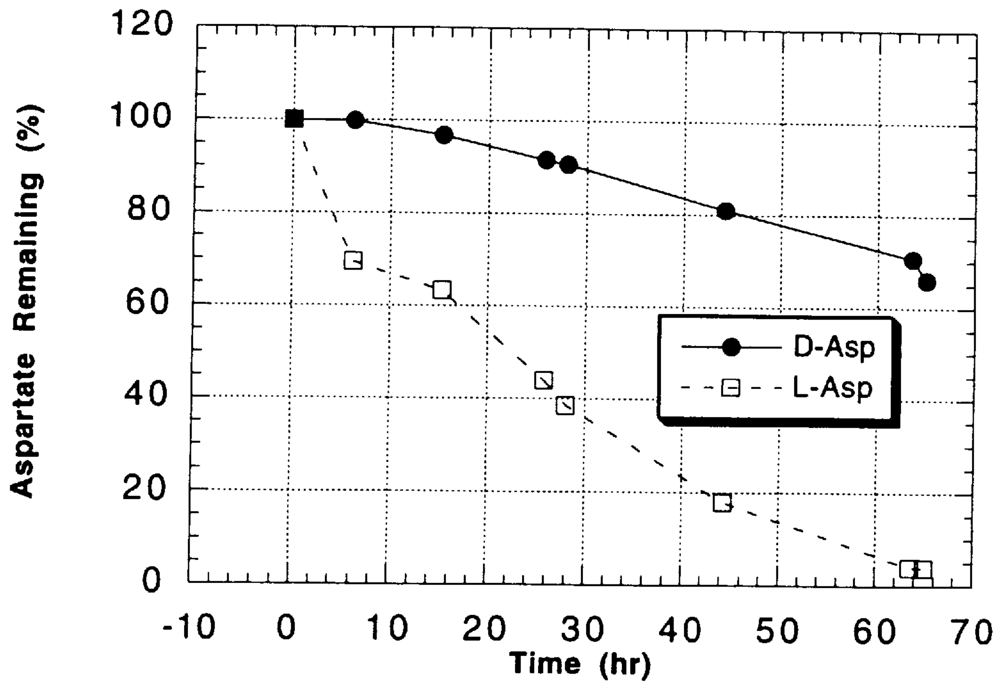
FIG. 4 shows the activity of previously used L-aspartate-α-decarboxylase enzyme on a fresh D,L-aspartate substrate solution.

The data in Table 3 are also graphically represented in FIG. 4. These results show that even after one cycle, the L-aspartate-α-decarboxylase still remains active, thus indicating that this biocatalyst can be recycled.

EXAMPLE 6

D/L-aspartate as Substrate for Various Enzyme Cell Loads 1.0M D/L-aspartate was tested as a substrate for two enzyme cell loads, 100 g/l cells, referred to here as reaction "A", and 50 g/l cells, referred to here as reaction "B".

133.1 g of D/L-aspartic acid was dissolved in approximately 600 ml deionized $H_2O$ and pH was adjusted to 7.0 with NaOH, using 100 ml of 10N NaOH and a small amount of 1.0N NaOH. The substrate for reaction A was brought to 963 ml with deionized $H_2O$. The reaction was started with 137 ml cells that were stored in the cold room. For reaction B, the substrate was brought to a volume of 981.5 ml. The reaction was started with 65.0 ml cells.

Both reactions were carried out in 2 L fermentors at pH 7.0 without constant adjustments and at 37° C. Samples were removed over time, centrifuged and the supernatant fluid was diluted and submitted for D- and L-aspartic acid HPLC analysis. Table 4 shows the results of reaction A and Table 5 shows the results of reaction B.

TABLE 4

| | Time (hr) | D-Asp (mg/ml) | D-Asp (%) | L-Asp (mg/ml) | L-Asp (%) |
|---|---|---|---|---|---|
| 0 | 0.0000 | 53.600 | 100.00 | 54.850 | 100.00 |
| 1 | 2.0000 | 50.680 | 94.552 | 49.340 | 89.954 |
| 2 | 4.5000 | 44.920 | 83.806 | 50.710 | 92.452 |
| 3 | 7.0000 | 42.260 | 78.843 | 50.230 | 91.577 |
| 4 | 22.500 | 35.680 | 66.567 | 54.490 | 99.344 |
| 5 | 24.000 | 34.420 | 64.216 | 50.780 | 92.580 |
| 6 | 31.000 | 32.660 | 60.933 | 51.450 | 93.801 |
| 7 | 37.500 | 27.950 | 52.146 | 53.850 | 98.177 |
| 8 | 47.000 | 20.710 | 38.638 | 52.370 | 95.479 |
| 9 | 50.500 | 18.490 | 34.496 | 51.080 | 93.127 |
| 10 | 53.800 | 13.730 | 25.616 | 46.500 | 84.777 |
| 11 | 58.000 | 13.410 | 25.019 | 50.040 | 91.231 |
| 12 | 70.000 | 6.1300 | 11.437 | 52.400 | 95.533 |
| 13 | 72.000 | 5.3900 | 10.056 | 50.430 | 91.942 |

TABLE 5

| | Time (hr) | D-Asp (mg/ml) | D-Asp (%) | L-Asp (mg/ml) | L-Asp (%) |
|---|---|---|---|---|---|
| 0 | 0.0000 | 56.730 | 100.00 | 57.440 | 100.00 |
| 1 | 2.0000 | 52.420 | .92.403 | 53.770 | 93.611 |
| 2 | 4.5000 | 51.340 | 90.499 | 52.310 | 91.069 |

TABLE 5-continued

| | Time (hr) | D-Asp (mg/ml) | D-Asp (%) | L-Asp (mg/ml) | L-Asp (%) |
|---|---|---|---|---|---|
| 3 | 7.0000 | 50.470 | 88.965 | 53.860 | 93.767 |
| 4 | 22.500 | 44.260 | 78.019 | 53.650 | 93.402 |
| 5 | 24.000 | 44.280 | 78.054 | 53.460 | 93.071 |
| 6 | 31.000 | 40.590 | 71.549 | 51.740 | 90.077 |
| 7 | 37.500 | 38.650 | 68.130 | 55.000 | 95.752 |
| 8 | 47.000 | 35.420 | 62.436 | 53.410 | 92.984 |
| 9 | 50.500 | 34.920 | 61.555 | 54.310 | 94.551 |
| 10 | 53.800 | 31.780 | 56.020 | 55.060 | 95.857 |
| 11 | 58.000 | 30.860 | 54.398 | 53.420 | 93.001 |
| 12 | 70.000 | 24.300 | 42.834 | 54.060 | 94.116 |
| 13 | 72.000 | 26.830 | 47.294 | 54.230 | 94.412 |

Figure 5:
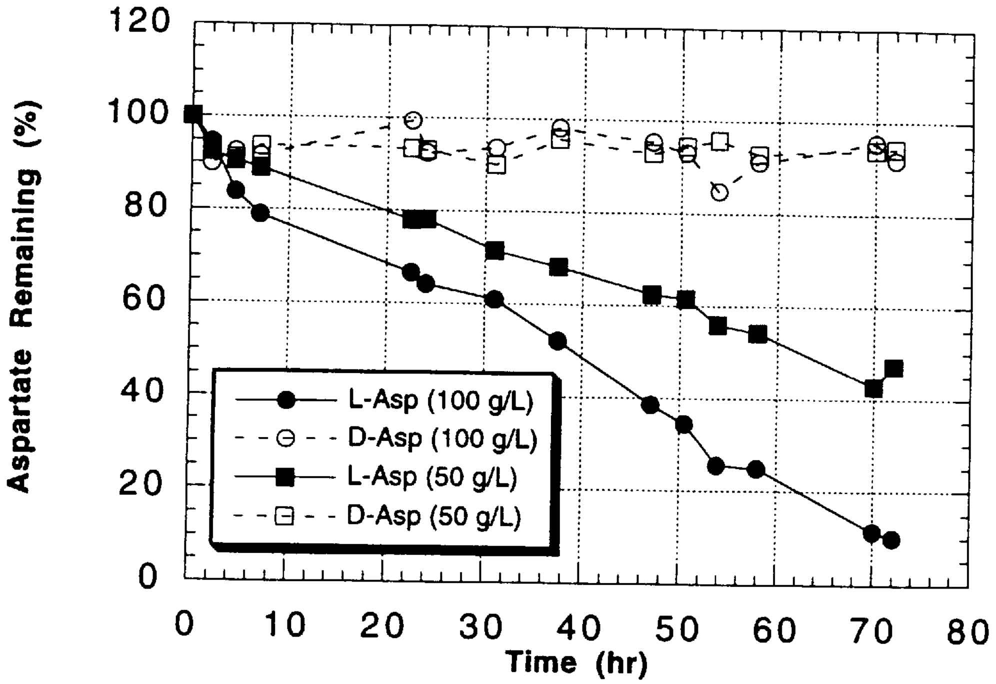
FIG. 5 shows the activity of L-aspartate-α-decarboxylase enzyme different loads, 50 g/l and 100 g/l, on a 1.0M solution of D,L-aspartate.

The data in Tables 4 and 5 are graphically presented in FIG. 5. Results show that the conversion rates for 100 g/l are faster than with 50 g/l. However, the rate at a substrate concentration of 1.0M D/L-aspartate is slower that at 0.5M. (See Example 3 and FIG. 2). Also, at 1.0M substrate, after 72.0 hours, the L-aspartate was reduced to 5.39 mg/ml from a starting concentration of 53.6 mg/ml, a 90% reduction.

EXAMPLE 7

L-aspartate-α-decarboxylase $NH_4OH$ Neutralized Substrate

This Example shows the effect of neutralizing the substrate, D/L-aspartate, with $NH_4OH$ instead of NaOH as done in the prior examples. Cells were stored frozen at −80° C. 133.1 g (1 mol) D/L-aspartic acid was dissolved in approximately 600 ml deionized $H_2O$ and adjusted to a pH of about 7 with concentrated $NH_4OH$. The final volume of substrate was brought to 963 ml to which was added 137 ml cells, freshly thawed. The mixture was placed in the 2 L fermentor and the temperature adjusted to 37° C. No automatic pH control was used, however, the pH was monitored as samples were removed and the pH adjusted with 50% $NH_4OH$. Samples, approximately 1 ml, were removed periodically, centrifuged, and the supernatant fluid was stored frozen prior to diluting and HPLC analysis.

TABLE 6

| | Time (hr) | D-Asp (mg/ml) | D-Asp (%) | L-Asp (mg/ml) | L-Asp (%) |
|---|---|---|---|---|---|
| 0 | 0.0000 | 55.260 | 100.00 | 55.740 | 100.00 |
| 1 | 3.0000 | 54.670 | 98.932 | 53.380 | 95.766 |
| 2 | 6.0000 | 49.100 | 88.853 | 56.370 | 101.13 |
| 3 | 9.0000 | 47.810 | 86.518 | 56.680 | 101.69 |
| 4 | 19.000 | 43.490 | 78.701 | 59.270 | 106.33 |
| 5 | 23.500 | 39.120 | 70.793 | 54.930 | 98.547 |
| 6 | 28.000 | 36.290 | 65.671 | 52.620 | 94.403 |

TABLE 6-continued

| | Time (hr) | D-Asp (mg/ml) | D-Asp (%) | L-Asp (mg/ml) | L-Asp (%) |
|---|---|---|---|---|---|
| 7 | 32.500 | 33.540 | 60.695 | 50.900 | 91.317 |
| 8 | 43.000 | 30.370 | 54.958 | 53.520 | 96.017 |
| 9 | 49.000 | 21.580 | 39.052 | 51.i00 | 91.676 |

Figure 6:
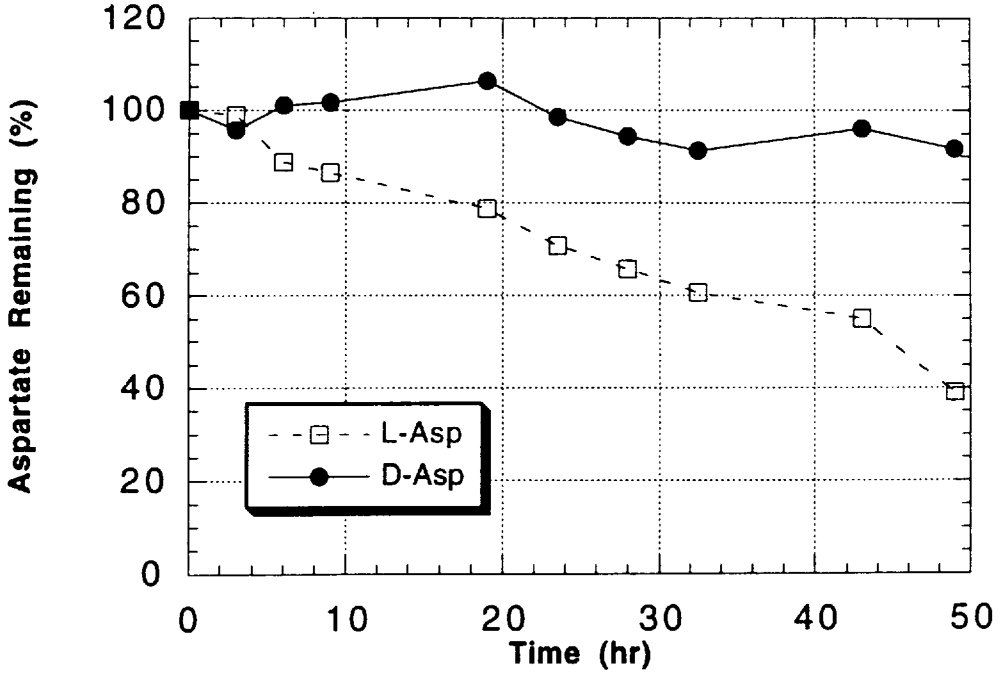
FIG. 6 shows the activity of L-aspartate-α-decarboxylase enzyme on $NH_4OH$-neutralized D,L-aspartate substrate.

The data in Table 6 is presented graphically in FIG. 6. The rate of L-Asp utilization is shown to be slower with the $NH_4^+$ salt as compared to the $Na^+$ salt.

EXAMPLE 8

Activity of L-aspartate-α-decarboxylase towards D/L-glutamate and D/L-alanine This Example shows the activity of L-aspartate-α-decarboxylase towards two potential amino acid substrates, D/L-glutamate and D/L-alanine. D/L-aspartate was run as a control.

Substrates were prepared by dissolving solid amino acid racemate in approximately 75 ml deionized $H_2O$ and adjusting the pH to 7.0 with 10N NaOH. The volume was then brought to 100 ml with deionized $H_2O$. The cells used were stored frozen for about 1 month and then thawed and stored in a refrigerator for about 1 month prior to running the experiments.

The reaction was run the same as described in the prior Examples. Samples of supernatant fluid, approximately 0.20 ml, were removed over time, centrifuged and stored frozen before analysis by HPLC as described in the prior Examples. Table 7 shows the results of the reactions.

TABLE 7

| | Time (hr) | L-Glu (mg/ml) | D-Glu (mg/ml) | L-Ala (mg/ml) | D-Ala (mg/ml) | L-Glu (%) | D-Glu (%) | L-Ala (%) | D-Ala (%) | L-Asp (mg/ml) | D-Asp (mg/ml) | L-Asp (%) | D-Asp (%) |
|---|---|---|---|---|---|---|---|---|---|---|---|---|---|
| 0 | 0 | 29.350 | 29.440 | 19.320 | 19.190 | 100.00 | 100.00 | 100.00 | 100.00 | 26.810 | 29.890 | 100.0 | 100.0 |
| 1 | 3.5 | 28.400 | 29.010 | 18.960 | 18.590 | 96.763 | 98.539 | 98.137 | 96.873 | 14.050 | 29.850 | 52.406 | 99.866 |
| 2 | 8.5 | 28.740 | 29.520 | 18.730 | 18.370 | 97.922 | 100.27 | 96.946 | 95.727 | 12.660 | 29.900 | 47.221 | 100.03 |
| 3 | 24 | 28.200 | 29.350 | 18.320 | 17.930 | 96.082 | 99.694 | 94.824 | 93.434 | 9.4700 | 29.740 | 35.323 | 99.498 |
| 4 | 55 | 28.000 | 29.840 | 17.830 | 17.580 | 95.400 | 101.36 | 92.288 | 91.610 | 0.3300 | 30.120 | 1.2309 | 100.77 |

Figure 7:
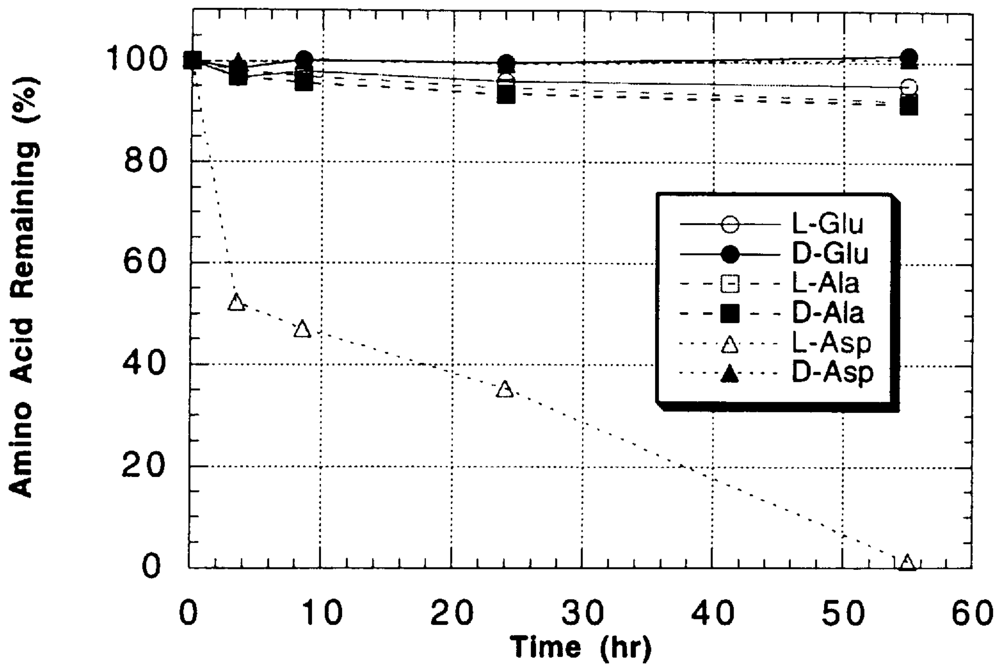
FIG. 7 compares the activity of L-aspartate-α-decarboxylase enzyme on various amino acid substrates, D,L-aspartate, D,L-glutamate and D,L-alanine.

The data in Table 7 are presented graphically in FIG. 7. The results show the specificity of the claimed method and enzyme preparation in that all isomers of substrates used except L-aspartic acid are stable up to 55 hours in the presence of the enzyme, indicating that L-aspartic acid is the only substrate for the enzyme. L-aspartic acid, as demonstrated throughout the specification, decreased to 1.23% of starting material.

EXAMPLE 9

Temperature Study

This Example shows the activity of the L-aspartate-α-decarboxylase reaction at 37° C., 45° C. and 50° C.

133.1 g (1 mol) of D/L-aspartic acid was dissolved in deionized $H_2O$ and the pH was adjusted to 7.0 with 10N NaOH, approximately 100 ml. Cells, freshly thawed from −80° C., were added to achieve a final concentration of 100 g/l. Three 2 L fermentors were each charged with 963 ml of substrate solution and 137 ml of cells and then heated to 37° C. and 45° C. while mixing at 300 rpm or heated to 50° C. while mixing at 450 rpm. Samples, approximately 1 ml, were removed over time and pH adjusted to 7.0 with either NaOH or HCl. After centrifugation to remove cells, the supernatant fluid was analyzed for both D- and L-aspartic acid.

Table 8 shows the results of the reaction at 37° C., Table 9 shows the results at 45° C. and Table 10 shows the results at 50° C.

TABLE 8

| | Time (hr) | D-Asp (mg/ml) | D-Asp (%) | L-Asp (mg/ml) | L-Asp (%) |
|---|---|---|---|---|---|
| 0 | 0.0000 | 55.000 | 100.00 | 53.700 | 100.00 |
| 1 | 2.5000 | 54.310 | 98.745 | 48.940 | 91.136 |
| 2 | 4.0000 | 54.440 | 98.982 | 47.600 | 88.641 |
| 3 | 6.0000 | 54.470 | 99.036 | 46.170 | 85.978 |
| 4 | 8.0000 | 54.760 | 99.564 | 44.810 | 83.445 |
| 5 | 10.000 | 55.840 | 101.53 | 42.120 | 78.436 |
| 6 | 12.000 | 56.760 | 103.20 | 42.120 | 78.462 |
| 7 | 20.000 | 55.460 | 100.84 | 35.960 | 66.965 |
| 8 | 24.000 | 55.390 | 100.71 | 34.840 | 64.879 |
| 9 | 29.000 | 53.990 | 98.164 | 28.040 | 54.078 |
| 10 | 34.000 | 53.440 | 97.164 | 28.040 | 54.078 |
| 11 | 44.000 | 52.960 | 96.291 | 21.670 | 40.354 |
| 12 | 48.000 | 52.940 | 96.255 | 18.440 | 34.339 |
| 13 | 68.000 | 49.940 | 90.800 | 5.9700 | 11.117 |
| 14 | 92.000 | 50.670 | 92.127 | 0.91500 | 1.7039 |

TABLE 9

| | Time (hr) | D-Asp (mg/ml) | D-Asp (%) | L-Asp (mg/ml) | L-Asp (%) |
|---|---|---|---|---|---|
| 0 | 0.000 | 55.280 | 100.00 | 54.410 | 100.00 |
| 1 | 2.5000 | 54.820 | 99.168 | 50.i00 | 92.079 |
| 2 | 4.0000 | 53.960 | 97.612 | 47.110 | 86.583 |
| 3 | 6.0000 | 53.460 | 96.708 | 43.130 | 79.269 |
| 4 | 8.0000 | 54.040 | 97.757 | 39.310 | 72.248 |
| 5 | 10.000 | 54.870 | 99.258 | 36.800 | 67.635 |
| 6 | 12.000 | 54.060 | 97.793 | 34.540 | 63.481 |
| 7 | 20.000 | 52.360 | 94.718 | 24.690 | 45.378 |
| 8 | 24.000 | 51.310 | 92.818 | 23.210 | 42.658 |
| 9 | 29.000 | 53.830 | 97.377 | 21.700 | 39.882 |
| 10 | 34.000 | 52.880 | 95.658 | 19.310 | 35.490 |
| 11 | 44.000 | 53.640 | 97.033 | 15.800 | 29.039 |
| 12 | 48.000 | 52.730 | 95.387 | 16.700 | 30.822 |
| 13 | 68.000 | 53.560 | 96.889 | 16.050 | 29.498 |
| 14 | 92.000 | 53.560 | 96.889 | 13.370 | 24.573 |

TABLE 10

| | Time (hr) | D-Asp (mg/ml) | D-Asp (%) | L-Asp (mg/ml) | L-Asp (%) |
|---|---|---|---|---|---|
| 0 | 0.000 | 54.89 | 48.47 | 100.0 | 100.0 |
| 1 | 1.000 | 54.30 | 52.78 | 98.93 | 108.9 |
| 2 | 3.000 | 58.01 | 40.61 | 105.7 | 83.78 |
| 3 | 5.0000 | 58.16 | 36.97 | 106.0 | 73.63 |
| 4 | 7.000 | 58.51 | 35.69 | 106.6 | 73.63 |
| 5 | 9.000 | 58.88 | 33.99 | 107.3 | 70.13 |
| 6 | 13.50 | 59.62 | 34.19 | 108.4 | 70.54 |
| 7 | 23.00 | 56.71 | 31.98 | 103.3 | 65.98 |
| 8 | 25.00 | 59.85 | 31.86 | 109.0 | 65.73 |
| 9 | 27.00 | 56.87 | 26.89 | 103.6 | 55.48 |
| 10 | 32.00 | 57.30 | 25.85 | 104.4 | 53.33 |
| 11 | 37.50 | 58.48 | 27.54 | 106.5 | 58.82 |
| 12 | 47.00 | 57.93 | 25.58 | 10s.s | 52.77 |
| 13 | 52.00 | 58.74 | 27.28 | 107.0 | 56.28 |
| 14 | 57.00 | 65.56 | 32.42 | 119.4 | 66.89 |
| 15 | 71.00 | 57.17 | 25.52 | 104.2 | 52.65 |
| 16 | 77.00 | 57.85 | 25.86 | 105.4 | 53.35 |
| 17 | 81.00 | 57.41 | 25.54 | 104.6 | 52.69 |
| 18 | 99.75 | 59.36 | 26.14 | 108.1 | 53.93 |

Figure 8:
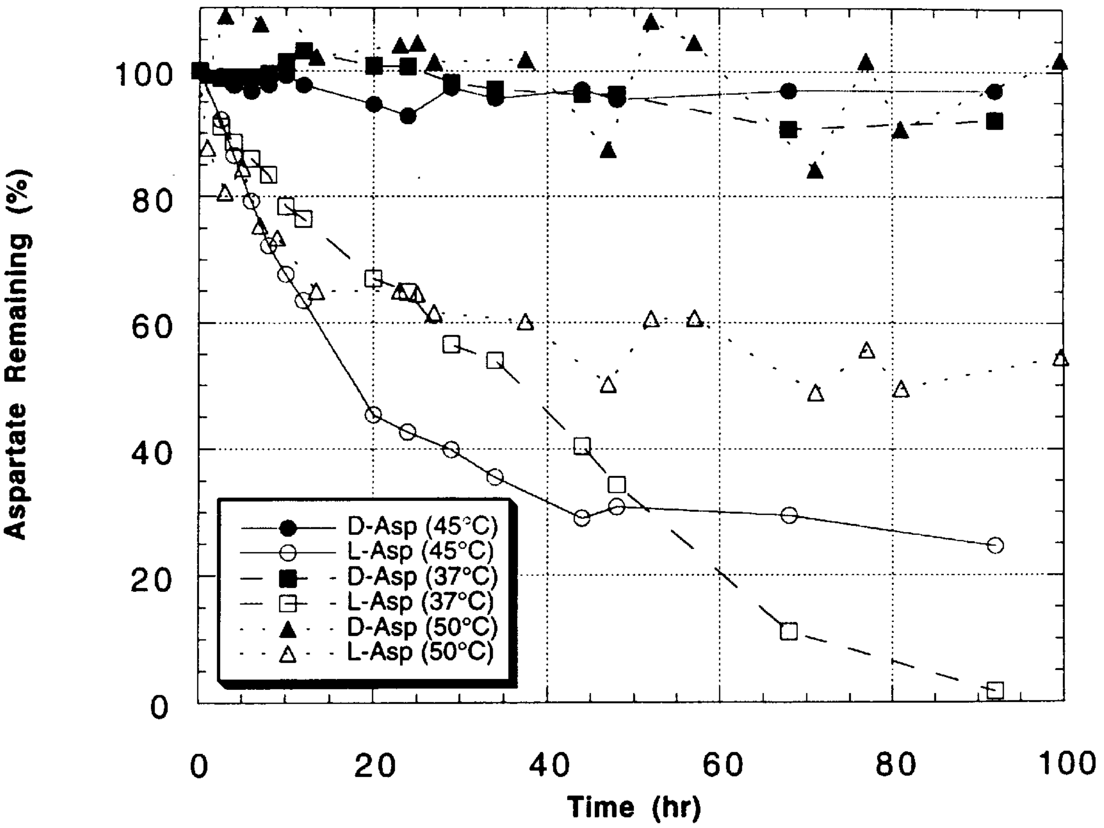
FIG. 8 compares the results of bioconversion of D,L-aspartate at temperatures of 37° C., 45° C. and 50° C.

The data from Tables 8, 9 and 10 are presented graphically together in FIG. 8. These results show that at all three temperatures, the D-isomer is stable. At 37° C., the L-isomer is almost completely consumed by 99.75 hours. At 45° C. and 50° C. the initial rate is shown to be increased with the higher temperature, but it appears that the enzyme becomes unstable and inactivates after an extended period of time. Although moderate temperatures are preferred for the claimed process and composition, the reaction rate can be increased by raising the reaction temperature.

What is claimed is:

1. A process for preparing D-aspartic acid which comprises contacting a solution of D,L-aspartic acid or a salt thereof with a composition comprising cells of a microorganism or extracts thereof, wherein the composition has an L-aspartate-α-decarboxylase activity of greater than 100 $\mu$mol L-aspartate used per hour per gram of cells, under appropriate conditions to produce D-aspartic acid and β-alanine.

2. The process of claim 1 wherein the composition has an L-aspartate-α-decarboxylase activity of about 100 to about 2000 $\mu$mol L-aspartate used per hour per gram of cells.

3. The process of claim 1 wherein the composition has an L-aspartate-α-decarboxylase activity of about 100 to about 1000 $\mu$mol L-aspartate used per hour per gram of cells.

4. The process of claim 1 wherein the composition comprises cells or extracts of cells of a microorganism transformed with the panD gene encoding L-aspartate-α-decarboxylase.

5. The process of claim 4 wherein the microorganism is a bacterium.

6. The process of claim 5 wherein the bacterium is selected from the group consisting of the bacteria of the genera Escherichia, Bacillus, Klebsiella, Pseudomonas, Salmonella, Proteus, Azotobacter, and Rhizobium.

7. The process of claim 6 wherein the bacterium is the strain *Escherichia coli* W3110.

8. The process of claim 4 wherein the panD gene is derived from a bacterium selected from the group consisting of *Escherichia coli* B, *Escherichia coli* K12, *Escherichia coli* NIHJ; *Escherichia coli* Tennessee; *Proteus vulgaris; Bacterium cadaveris; Azotobacter vinelandii; Rhizobium leguminosarum*; and *Rhizobium trifolii.*

9. The process of claim 8 wherein the bacterium is a strain of *Escherichia coli* K12.

10. The process of claim 1 wherein the composition comprises cells or extracts of cells of *Escherichia coli* NS3291 (ATCC Accession No. 98675).

11. The process of claim 1 wherein the contacting comprises incubation of the D,L-aspartic acid or salt thereof with the composition at a temperature of between about 4° C. and about 70° C. and a pH of between about 2 and about 12.

12. The process of claim 11 wherein the contacting comprises incubation of the D,L-aspartic acid or salt thereof with the composition at ambient temperature and a pH of approximately 7.0.

13. The process of claim 1 wherein the composition comprises cells or extracts of cells immobilized on an activated substrate.

14. The process of claim 13 wherein the activated substrate is chosen from the group consisting of porous glass, porous ceramics, bentonite, diatomaceous earth, charcoal, Sepharose and Sepharose derivatives, cellulose and cellulose derivatives, polyacrylamide, polyacrylamide derivatives, polyazetidine, alginate, carrageenan, and Chromosorb.

15. A process for preparing D-aspartic acid which comprises (a) preparing an aqueous solution of D,L-aspartic acid or salt thereof; (b) incubating the aqueous solution of D,L-aspartic acid or a salt thereof at a temperature of between about 4° C. and about 70° C. and a pH of between about 2 and about 12 with a composition comprising an L-aspartate-α-decarboxylase activity of greater than 100 μmol L-aspartate used per hour per gram of cells, and (c) recovering D-aspartic acid and β-alanine.

16. The process of claim 15 wherein the composition has an L-aspartate-α-decarboxylase activity of about 100 to about 2000 μmol L-aspartate used per hour per gram of cells.

17. The process of claim 15 wherein the composition has an L-aspartate-α-decarboxylase activity of about 100 to about 1000 μmol L-aspartate used per hour per gram of cells.

18. The process of claim 15 wherein the composition comprises cells or extracts of cells of an organism transformed with the panD gene encoding L-aspartate-α-decarboxylase.

19. The process of claim 17 wherein the organism is a bacterium.

20. The process of claim 19 wherein the bacterium is selected from group consisting of the bacteria of the genera Escherichia, Bacillus, Klebsiella, Pseudomonas, Salmonella, Proteus, Azotobacter, and Rhizobium.

21. The process of claim 20 wherein the bacterium is the strain *Escherichia coli* W3110.

22. The process of claim 18 wherein the panD gene is derived from a bacterium selected from the group consisting of *Escherichia coli* B, *Escherichia coli* K12, *Escherichia coli* NIHJ; *Escherichia coli* Tennessee; *Proteus vulgaris; Bacterium cadaveris; Azotobacter vinelandii; Rhizobium leguminosarum*; and *Rhizobium trifolii.*

23. The process of claim 22 wherein the bacterium is a strain of *Escherichia coli* K12.

24. The process of claim 18 wherein the composition comprises cells or extracts of cells of *E. coli* NS3291 (ATCC Accession No. 98675).

25. The process of claim 15 wherein the contacting comprises incubation of the D,L-aspartic acid or salt thereof with the composition at ambient temperature and a pH of approximately 7.0.

* * * * *

UNITED STATES PATENT AND TRADEMARK OFFICE

CERTIFICATE OF CORRECTION

PATENT NO. 5,834,259

DATED November 10, 1998

INVENTOR(S) Pantaleone et al

It is certified that error appears in the above-identified patent and that said Letters Patent is hereby corrected as shown below:

COLUMN 7

Line 42, "Pad" should read --panD--; and
Line 47, "Newhaven," should read --New Haven,--.

COLUMN 10:

Line 27, "short hand" should read --shorthand--.

COLUMN 11:

Line 44, "is" should read --are--.

COLUMN 14:

TABLE 6-continued, "51.i00" should read -- 51,100--.

UNITED STATES PATENT AND TRADEMARK OFFICE

CERTIFICATE OF CORRECTION

PATENT NO. 5,834,259

DATED November 10, 1998

INVENTOR(S) Pantaleone et al

It is certified that error appears in the above-identified patent and that said Letters Patent is hereby corrected as shown below:

COLUMN 15:

TABLE 9, "5.i00" should read --50.100--.
TABLE 10, "10s.s" should read --105.5--.

Signed and Sealed this

Seventeenth Day of October, 2000

Attest:

Q. TODD DICKINSON

Attesting Officer

*Director of Patents and Trademarks*